(12) United States Patent
Greenfield et al.

(10) Patent No.: US 7,429,582 B2
(45) Date of Patent: Sep. 30, 2008

(54) DIHYDRO[1,4]OXAZINO[2,3,4-HI]INDAZOLE DERIVATIVES AS 5-HYDROXYTRYPTAMINE-6 LIGANDS AND USE THEREOF IN THE TREATMENT OF ATTENTION DEFICIT DISORDERS

(75) Inventors: Alexander Alexei Greenfield, West Windsor, NJ (US); Cristina Grosanu, Keansburg, NJ (US); Hassan Mahmoud Elokdah, North Wales, PA (US); Albert Jean Robichaud, Ringoes, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/786,314

(22) Filed: Apr. 11, 2007

(65) Prior Publication Data
US 2007/0244105 A1 Oct. 18, 2007

Related U.S. Application Data

(60) Provisional application No. 60/791,477, filed on Apr. 12, 2006.

(51) Int. Cl.
*C07D 498/04* (2006.01)
*A61K 31/5365* (2006.01)

(52) U.S. Cl. .................................. 514/230.2; 544/101
(58) Field of Classification Search .............. 544/101; 514/230.2
See application file for complete search history.

(56) References Cited

U.S. PATENT DOCUMENTS

2004/0024210 A1  2/2004  Johansson et al.
2004/0138286 A1  7/2004  Imazaki et al.
2007/0037802 A1  2/2007  Elokdah et al.

FOREIGN PATENT DOCUMENTS

| WO | WO 98/11112 | 3/1998 |
|---|---|---|
| WO | WO 99/20633 | 4/1999 |
| WO | WO 00/63215 | 10/2000 |

OTHER PUBLICATIONS

Russell MG and Dias R. (Curr. Top. Med. Chem, Jun. 2002; 2(6):643-54).*
Chalmers (TiPs vol. 17, pp. 166-172 Apr. 1996).*

* cited by examiner

*Primary Examiner*—Kahsay T Habte
(74) *Attorney, Agent, or Firm*—Gloria Szakiel; Andrea Dorigo; Scott Larsen

(57) ABSTRACT

The present invention provides a compound of formula I and the use thereof for the treatment of a central nervous system disorder related to or affected by the 5-HT6 receptor

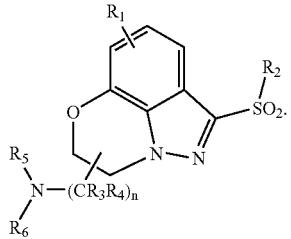

(I)

16 Claims, No Drawings

DIHYDRO[1,4]OXAZINO[2,3,4-HI]INDAZOLE DERIVATIVES AS 5-HYDROXYTRYPTAMINE-6 LIGANDS AND USE THEREOF IN THE TREATMENT OF ATTENTION DEFICIT DISORDERS

This application claims the benefit under 35 U.S.C. §119 (e) to co-pending U.S. provisional application No. 60/791,477, filed Apr. 12, 2006, which is hereby incorporated by reference in its entirety.

BACKGROUND OF THE INVENTION

Serotonin (5-hydroxytryptamine) (5-HT) receptors play a critical role in many physiological and behavioral functions in humans and animals. These functions are mediated through various 5-HT receptors distributed throughout the body. There are now approximately fifteen different human 5-HT receptor subtypes that have been cloned, many with well-defined roles in humans. One of the most recently identified 5-HT receptor subtypes is the 5-HT6 receptor, first cloned from rat tissue in 1993 (Monsma, F. J.; Shen, Y.; Ward, R. P.; Hamblin, M. W. *Molecular Pharmacology* 1993, 43, 320-327) and subsequently from human tissue (Kohen, R.; Metcalf, M. A.; Khan, N.; Druck, T.; Huebner, K.; Sibley, D. R. *Journal of Neurochemistry* 1996, 66, 47-56). The receptor is a G-protein coupled receptor (GPCR) positively coupled to adenylate cyclase (Ruat, M.; Traiffort, E.; Arrang, J-M.; Tardivel-Lacombe, L.; Diaz, L.; Leurs, R.; Schwartz, J-C. *Biochemical Biophysical Research Communications* 1993, 193, 268-276). The receptor is found almost exclusively in the central nervous system (CNS) areas both in rat and in human. In situ hybridization studies of the 5-HT6 receptor in rat brain using mRNA indicate principal localization in the areas of 5-HT projection including striatum, nucleus accumbens, olfactory tubercle, and hippocampal formation (Ward, R. P.; Hamblin, M. W.; Lachowicz, J. E.; Hoffman, B. J.; Sibley, D. R.; Dorsa, D. M. *Neuroscience* 1995, 64, 1105-1111).

There are many potential therapeutic uses for 5-HT6 ligands in humans based on direct effects and on indications from available scientific studies. These studies provided information including the localization of the receptor, the affinity of ligands with known in vivo activity, and results obtained from various animal studies conducted so far (Woolley, M. L.; Marsden, C. A.; Fone, K. C. F. *Current Drug Targets: CNS & Neurological Disorders* 2004, 3(1), 59-79).

One therapeutic use of modulators of 5-HT6 receptor function is in the enhancement of cognition and memory in human diseases such as Alzheimer's. The high levels of receptor found in important structures in the forebrain, including the caudate/putamen, hippocampus, nucleus accumbens, and cortex indicate a role for the receptor in memory and cognition since these areas are known to play a vital role in memory (Gerard, C.; Martres, M.-P.; Lefevre, K.; Miquel, M. C.; Verge, D.; Lanfumey, R.; Doucet, E.; Hamon, M.; El Mestikawy, S. *Brain Research*, 1997, 746, 207-219). The ability of known $5\text{-HT}_6$ receptor ligands to enhance cholinergic transmission also supported the cognition use (Bentley, J. C.; Boursson, A.; Boess, F. G.; Kone, F. C.; Marsden, C. A.; Petit, N.; Sleight, A. J. *British Journal of Pharmacology*, 1999, 126(7), 1537-1542). Studies have demonstrated that a known $5\text{-HT}_6$ selective antagonist significantly increased glutamate and aspartate levels in the frontal cortex without elevating levels of noradrenaline, dopamine, or 5-HT. This selective elevation of neurochemicals known to be involved in memory and cognition indicates the role $5\text{-HT}_6$ ligands play in cognition (Dawson, L. A.; Nguyen, H. Q.; Li, P. *British Journal of Pharmacology*, 2000, 130(1), 23-26). Animal studies of memory and learning with a known selective $5\text{-HT}_6$ antagonist found positive effects (Rogers, D. C.; Hatcher, P. D.; Hagan, J. J. *Society of Neuroscience, Abstracts* 2000, 26, 680). More recent studies have supported this finding in several additional animal models of cognition and memory including in a novel object discrimination model (King, M. V.; Sleight, A. J.; Wooley, M. L.; Topham, I. A.; Marsden, C. A.; Fone, K. C. F. *Neuropharmacology* 2004, 47(2), 195-204 and Wooley, M. L.; Marsden, C. A.; Sleight, A. J.; Fone, K. C. F. *Psychopharmacology*, 2003, 170(4), 358-367) and in a water maze model (Rogers, D. C.; Hagan, J. J. *Psychopharmacology*, 2001, 158(2), 114-119 and Foley, A. G.; Murphy, K. J.; Hirst, W. D.; Gallagher, H. C.; Hagan, J. J.; Upton, N.; Walsh, F. S.; Regan, C. M. *Neuropsychopharmacology* 2004, 29(1), 93-100).

A related therapeutic use for $5\text{-HT}_6$ ligands is the treatment of attention deficit disorders (ADD, also known as Attention Deficit Hyperactivity Disorder or ADHD) in both children and adults. Because $5\text{-HT}_6$ antagonists enhance the activity of the nigrostriatal dopamine pathway and because ADHD has been linked to abnormalities in the caudate (Ernst, M; Zametkin, A. J.; Matochik, J. H.; Jons, P. A.; Cohen, R. M. *Journal of Neuroscience* 1998, 18(15), 5901-5907), $5\text{-HT}_6$ antagonists attenuate attention deficit disorders.

Early studies examining the affinity of various CNS ligands with known therapeutic utility or a strong structural resemblance to known drugs implicates $5\text{-HT}_6$ ligands in the treatment of schizophrenia and depression. For example, clozapine (an effective clinical antipsychotic) has high affinity for the $5\text{-HT}_6$ receptor subtype. Also, several clinical antidepressants have high affinity for the receptor as well and act as antagonists at this site (Branchek, T. A.; Blackburn, T. P. *Annual Reviews in Pharmacology and Toxicology* 2000, 40, 319-334).

Further, recent in vivo studies in rats indicate that $5\text{-HT}_6$ modulators are useful in the treatment of movement disorders including epilepsy (Stean, T.; Routledge, C.; Upton, N. *British Journal of Pharmacology* 1999, 127 Proc. Supplement 131P and Routledge, C.; Bromidge, S. M.; Moss, S. F.; Price, G. W.; Hirst, W.; Newman, H.; Riley, G.; Gager, T.; Stean, T.; Upton, N.; Clarke, S. E.; Brown, A. M. *British Journal of Pharmacology* 2000, 130(7), 1606-1612).

Therefore, it is an object of this invention to provide compounds which are useful as therapeutic agents in the treatment of a variety of central nervous system disorders related to or affected by the 5-HT6 receptor.

It is another object of this invention to provide therapeutic methods and pharmaceutical compositions useful for the treatment of central nervous system disorders related to or affected by the 5-HT6 receptor.

It is a feature of this invention that the compounds provided may also be used to further study and elucidate the 5-HT6 receptor.

SUMMARY OF THE INVENTION

The present invention provides a dihydro[1,4]oxazino[2,3,4-hi]indazole compound of formula I

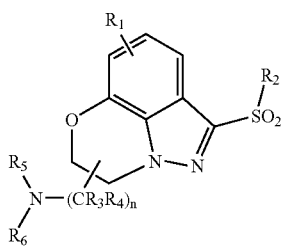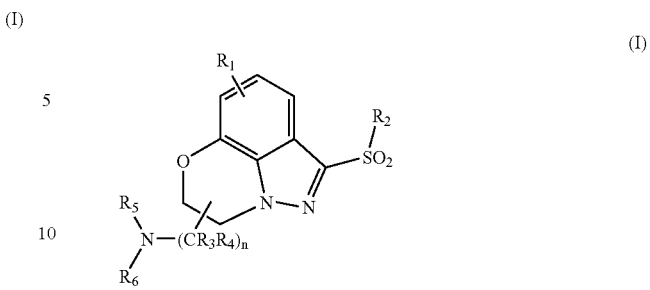

wherein
R₁ is H, halogen, CN, NO₂, OR₇, alkyl or haloalkyl;
R₂ is an alkyl, cycloalkyl, aryl or heteroaryl group each group optionally substituted or an optionally substituted 8- to 13-membered bicyclic or tricyclic ring system having a N atom at the bridgehead and optionally containing 1, 2 or 3 additional heteroatoms selected from N, O or S;
R₃ and R₄ are each independently H, or an optionally substituted alkyl group;
n is an integer of 1, 2, 3, 4, or 5;
R₅ and R₆ are each independently H or an alkyl, alkenyl, alkynyl or cycloalkyl, group each group optionally substituted or R₅ and R₆ may be taken together with the atom to which they are attached to form an optionally substituted 3- to 7-membered ring optionally containing an additional heteroatom selected from N, O or S; and
R₇ is H, alkyl or haloalkyl; or a stereoisomer thereof or a pharmaceutically acceptable salt thereof.

The present invention also provides methods and compositions useful for the therapeutic treatment of central nervous system disorders related to or affected by the 5-HT6 receptor.

DETAILED DESCRIPTION OF THE INVENTION

The 5-hydroxytryptamine-6 (5-HT6) receptor has been identified by molecular cloning. Its ability to bind a wide range of therapeutic compounds used in psychiatry, coupled with its intriguing distribution in the brain has stimulated significant interest in new compounds which are capable of interacting with or affecting said receptor. Significant efforts are being made to understand the role of the 5-HT6 receptor in psychiatry, cognitive dysfunction, motor function and control, memory, mood and the like. To that end, compounds which demonstrate a binding affinity for the 5-HT6 receptor are earnestly sought both as an aid in the study of the 5-HT6 receptor and as potential therapeutic agents in the treatment of central nervous system disorders, for example see C. Reavill and D. C. Rogers, Current Opinion in Investigational Drugs, 2001, 2(1):104-109, Pharma Press Ltd and Woolley, M. L.; Marsden, C. A.; Fone, K. C. F. *Current Drug Targets: CNS & Neurological Disorders* 2004, 3(1), 59-79.

Surprisingly, it has now been found that dihydro[1,4]oxazino[2,3,4-hi]indazole compounds of formula I demonstrate 5-HT6 affinity along with significant sub-type selectivity. Advantageously, said formula I compounds are effective therapeutic agents for the treatment of central nervous system (CNS) disorders associated with or affected by the 5-HT6 receptor. Accordingly, the present invention provides a dihydro[1,4]oxazino[2,3,4-hi]indazole compound of formula I wherein
R₁ is H, halogen, CN, NO₂, OR₇, alkyl or haloalkyl;
R₂ is an alkyl, cycloalkyl, aryl or heteroaryl group each group optionally substituted or an optionally substituted 8- to 13-membered bicyclic or tricyclic ring system having a N atom at the bridgehead and optionally containing 1, 2 or 3 additional heteroatoms selected from N, O or S;
R₃ and R₄ are each independently H, or an optionally substituted alkyl group;
n is an integer of 1, 2, 3, 4, or 5;
R₅ and R₆ are each independently H or an alkyl, alkenyl, alkynyl or cycloalkyl, group each group optionally substituted or R₅ and R₆ may be taken together with the atom to which they are attached to form an optionally substituted 3- to 7-membered ring optionally containing an additional heteroatom selected from N, O or S; and
R₇ is H, alkyl or haloalkyl; or a stereoisomer thereof or a pharmaceutically acceptable salt thereof.

Preferred compounds of the invention are those compounds of formula I wherein n is 1. Another group of preferred compounds is those formula I compounds wherein R₂ is an optionally substituted aryl or heteroaryl group or an optionally substituted 8- to 13-membered bicyclic or tricyclic ring system having a N atom at the bridgehead and optionally containing 1, 2 or 3 additional heteroatoms selected from N, O or S. Also preferred are those formula I compounds wherein R₅ and R₆ are each independently H or alkyl or R₅ and R₆ are taken together with the atom to which they are attached to form an optionally substituted 3- to 7-membered ring.

More preferred compounds of the invention are those compounds of formula I wherein n is 1 and R₁ is H, halogen or C₁-C₃ alkyl. Another group of more preferred compounds is those compounds of formula I wherein n is 1; R₂ is an optionally substituted aryl or heteroaryl group; and R₃ and R₄ are H. A further group of more preferred compounds are those compounds of formula I wherein n is 1; R₂ is naphthyl; and R₅ and R₆ are each independently H or alkyl or R₅ and R₆ are taken together with the atom to which they are attached to form an optionally substituted 3- to 5-membered ring.

Among the preferred compounds of the invention are:
N,N-dimethyl-1-[6-(1-naphthylsulfonyl)-2,3-dihydro[1,4]oxazino[2,3,4-hi]indazol-2-yl]-methanamine;
6-(1-naphthylsulfonyl)-2-(pyrrolidin-1-1ylmethyl)-2,3-dihydro[1,4]oxazino[2,3,4-hi]-indazole;
6-(1-naphthylsulfonyl)-2-(piperidin-1-1ylmethyl)-2,3-dihydro[1,4]oxazino[2,3,4-hi]-indazole;
1-[6-(1-naphthylsulfonyl)-2,3-dihydro[1,4]oxazino[2,3,4-hi]indazol-2-yl]-methanamine;

a stereoisomer thereof; or a pharmaceutically acceptable salt thereof.

An optionally substituted moiety may be substituted with one or more substituents. The substituent groups, which are optionally present, may be one or more of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy, heterocyclyl or cycloalkyl groups, preferably halogen atoms or lower alkyl or lower haloalkyl groups. Unless otherwise specified, typically, 1-3 substituents may be present.

The term "halogen", as used herein, designates fluorine, chlorine, bromine, and iodine.

As used herein, the term "alkyl" includes both ($C_1$-$C_{10}$) straight chain and ($C_3$-$C_{12}$) branched-chain (unless defined otherwise) monovalent saturated hydrocarbon moiety. Examples of saturated hydrocarbon alkyl moieties include, but are not limited to, chemical groups such as methyl, ethyl, n-propyl, isopropyl, n-butyl, tert-butyl, isobutyl, sec-butyl; higher homologs such as n-pentyl, n-hexyl, and the like. Specifically included within the definition of "alkyl" are those alkyl groups that are optionally substituted. Suitable alkyl substitutions include, but are not limited to, CN, OH, halogen, phenyl, carbamoyl, carbonyl, alkoxy or aryloxy.

As used herein, the term "haloalkyl" designates a $C_nH_{2n+1}$ group having from one to 2n+1 halogen atoms which may be the same or different. Examples of haloalkyl groups include $CF_3$, $CH_2Cl$, $C_2H_3BrCl$, $C_3H_5F_2$, or the like.

The term "alkenyl", as used herein, refers to either a ($C_2$-$C_8$) straight chain or ($C_3$-$C_{10}$) branched-chain monovalent hydrocarbon moiety containing at least one double bond. Such hydrocarbon alkenyl moieties may be mono or polyunsaturated, and may exist in the E or Z configurations. The compounds of this invention are meant to include all possible E and Z configurations. Examples of mono or polyunsaturated hydrocarbon alkenyl moieties include, but are not limited to, chemical groups such as vinyl, 2-propenyl, isopropenyl, crotyl, 2-isopentenyl, butadienyl, 2-(butadienyl), 2,4-pentadienyl, 3-(1,4-pentadienyl), or the like.

Similarly, the term "alkynyl", as used herein, refers to either a ($C_2$-$C_8$) straight chain or ($C_3$-$C_{10}$) branched-chain monovalent hydrocarbon moiety containing at least one triple bond. Such hydrocarbon alkenyl moieties may be mono or polyunsaturated, and may exist in the E or Z configurations. The compounds of this invention are meant to include all possible E and Z configurations. Examples of mono or polyunsaturated hydrocarbon alkynyl moieties include, but are not limited to, chemical groups such as 2-propynyl, 3-pentynyl, or the like.

The term "cycloalkyl", as used herein, refers to a monocyclic, bicyclic, tricyclic, fused, bridged, or spiro monovalent saturated hydrocarbon moiety of 3-10 carbon atoms. Examples of cycloalkyl moieties include, but are not limited to, chemical groups such as cyclopropyl, cyclobutyl, cyclopentyl, cyclohexyl, cycloheptyl, norbornyl, adamantyl, spiro [4.5]decanyl, or the like.

The term "cycloheteroalkyl" as used herein designates a five- to seven-membered cycloalkyl ring system containing 1, 2 or 3 heteroatoms, which may be the same or different, selected from N, O or S and optionally containing one double bond. Exemplary of the cycloheteroalkyl ring systems included in the term as designated herein are the following rings wherein X is NR, O or S and R is H or an optional substituent as defined hereinbelow.

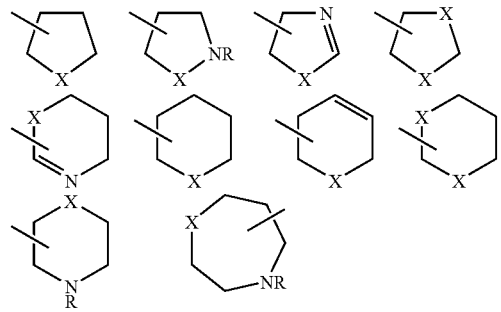

The term "aryl", as used herein, refers to an aromatic carbocyclic moiety of up to 20 carbon atoms, which may be a single ring (monocyclic) or multiple rings (bicyclic, up to three rings) fused together or linked covalently. Examples of aryl moieties include, but are not limited to, phenyl, 1-naphthyl, 2-naphthyl, biphenyl, anthryl, phenanthryl, fluorenyl, indanyl, biphenylenyl, acenaphthenyl, acenaphthylenyl, and the like.

The term "heteroaryl" as used herein designates an aromatic heterocyclic ring system, which may be a single ring (monocyclic) or multiple rings (bicyclic, up to three rings) fused together or linked covalently. Preferably, heteroaryl is a 5- to 6-membered ring. The rings may contain from one to four hetero atoms selected from N, O or S, wherein the nitrogen or sulfur atom is optionally oxidized, or the nitrogen atom is optionally quarternized. Examples of heteroaryl moieties include, but are not limited to, furan, thiophene, pyrrole, pyrazole, imidazole, oxazole, isoxazole, thiazole, isothiazole, oxadiazole, triazole, pyridine, pyrimidine, pyrazine, pyridazine, benzimidazole, benzoxazole, benzisoxazole, benzothiazole, benzofuran, benzothiophene, thianthrene, dibenzofuran, dibenzothiophene, indole, indazole, quinoline, isoquinoline, quinazoline, quinoxaline, purine, or the like.

Exemplary of the 8- to 13-membered bicyclic or tricyclic ring systems having a N atom at the bridgehead and optionally containing 1, 2 or 3 additional heteroatoms selected from N, O or S included in the term as designated herein are the following ring systems wherein W is NR', O or S; and R' is H or an optional substituent as described hereinbelow:

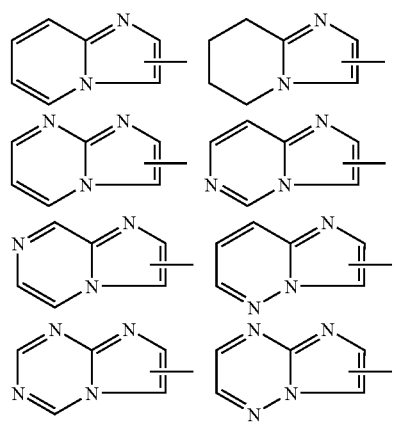

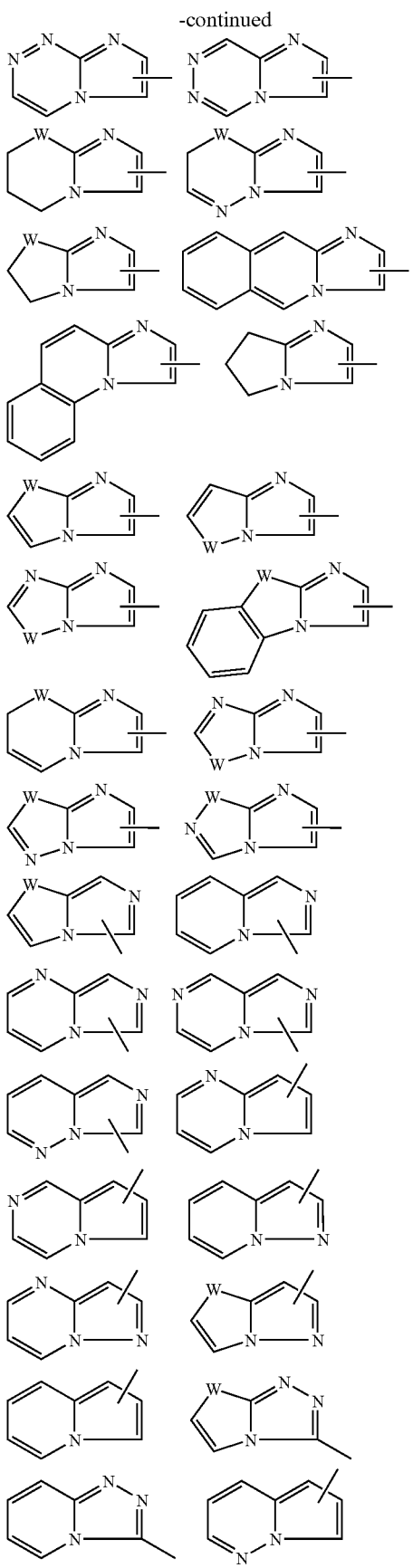

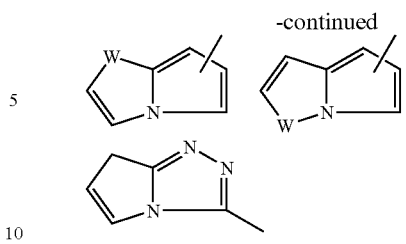

While shown without respect to stereochemistry, compounds of formula I include all stereochemical forms of the structure; i.e., the R and S configurations for each asymmetric center. Therefore, single stereochemical isomers as well as enantiomeric and diastereomeric mixtures of the present compounds are within the scope of the invention. The compounds of this invention may contain one or more asymmetric centers and may thus give rise to optical isomers and diastereomers. The present invention includes such optical isomers and diastereomers; as well as the racemic and resolved, enantiomerically pure R and S stereoisomers; as well as other mixtures of the R and S stereoisomers and pharmaceutically acceptable salts thereof. Where a stereoisomer is preferred, it may in some embodiments be provided substantially free of the corresponding enantiomer. Thus, an enantiomer substantially free of the corresponding enantiomer refers to a compound that is isolated or separated via separation techniques or prepared free of the corresponding enantiomer. "Substantially free", as used herein, means that the compound is made up of a significantly greater proportion of one steriosomer, preferably less than about 50%, more preferably less than about 75%, and even more preferably less than about 90%.

Formula I structures depicted herein are also meant to include compounds which differ only in the presence of one or more isotopically enriched atoms. For example, compounds having the present structure except for the replacement of a hydrogen by a deuterium or tritium, or the replacement of a carbon by a $^{13}C$- or $^{14}C$-enriched carbon are within the scope of this invention.

The compounds of the present invention may be converted to salts, in particular pharmaceutically acceptable salts using art recognized procedures. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-tert-butyl-, diethyl-, diisopropyl-, triethyl-, tributyl- or dimethylpropylamine, or a mono-, di-, or trihydroxy lower alkylamine, for example mono-, di- or triethanolamine. Internal salts may furthermore be formed. The term "pharmaceutically acceptable salt", as used herein, refers to salts derived from organic and inorganic acids such as, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety.

Compounds of the invention include esters, carbamates or other conventional prodrug forms, which in general, are functional derivatives of the compounds of the invention and which are readily converted to the inventive active moiety in vivo. Correspondingly, the method of the invention embraces the treatment of the various conditions described hereinabove with a compound of formula I or with a compound which is not specifically disclosed but which, upon administration, converts to a compound of formula I in vivo.

Advantageously, the present invention also provides a convenient and effective process for the preparation of a compound of formula I which comprises reacting a compound of formula II with an amine of formula III, optionally in the presence of a solvent, to give the compound of formula I. The process is shown hereinbelow in flow diagram I wherein X is Cl, Br or I.

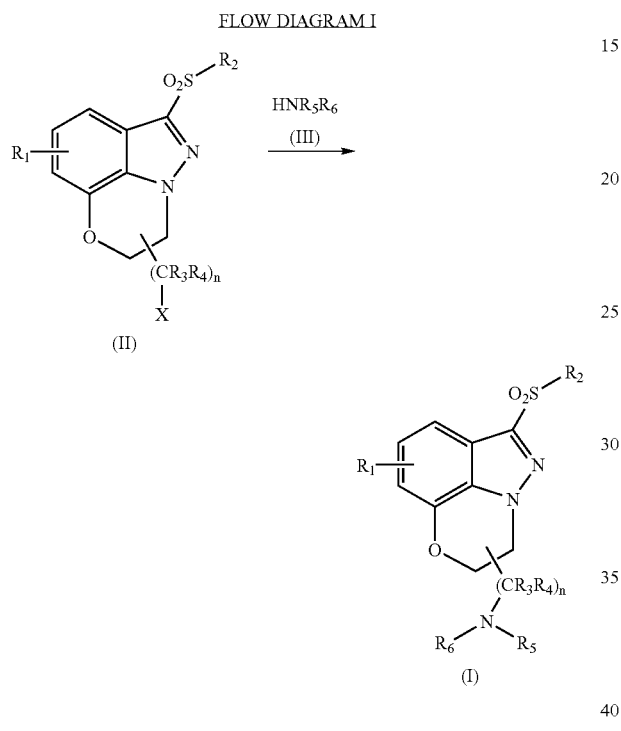

Solvents suitable for use in the process of the invention include dimethylsulfoxide, dimethyl formamide, dioxane, or the like, or a mixture thereof.

Compounds of formula II may be prepared using conventional synthetic methods and, if required, standard isolation or separation techniques. For example, compounds of formula II wherein n is 1 and the aminoalkyl moiety is attached in the 2-position (IIa) may be prepared by reacting an ortho-fluoronitrobenzene compound of formula IV with 1,3-dichloropropan-2-ol in the presence of a base such as lithium diisopropylamide (LDA) to form the compound of formula V; reacting the formula V compound with a chloromethanesulfonyl compound of formula VI in the presence of a base such as potassium t-butoxide to give the compound of formula VII; reducing the formula VII compound with a conventional reducing agent such as $H_2$ and a Palladium on Carbon catalyst to form the amino compound of formula VIII; cyclizing the formula VIII amine in the presence of $NaNO_2$ and HCl to give the indazole compound of formula IX; and reacting the formula IX indazole with triethylamine to give the desired dihydro-oxazinoindazole of formula IIa. The reaction is shown in flow diagram II.

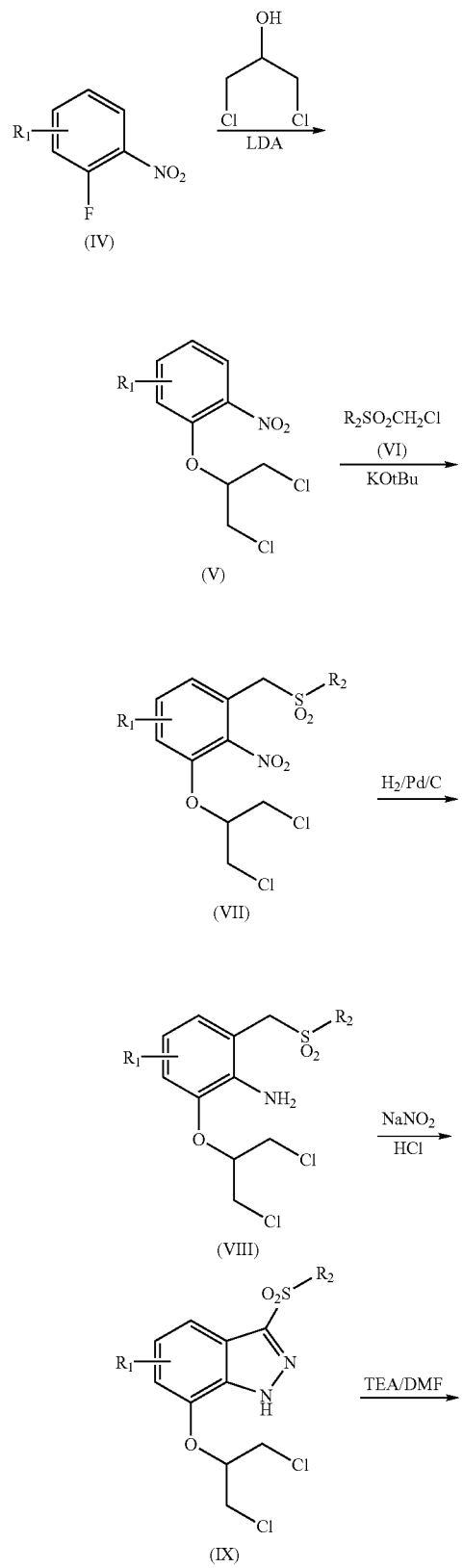

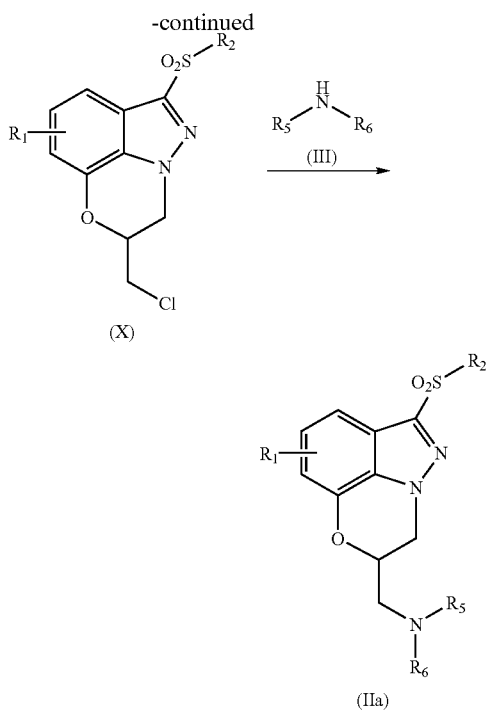

Advantageously, the formula I compounds of the invention are useful for the treatment of CNS disorders related to or affected by the 5-HT6 receptor including motor, mood, personality, behavioral, psychiatric, cognitive, neurodegenerative, or the like disorders, for example Alzheimer's disease, Parkinson's disease, attention deficit disorder, anxiety, epilepsy, depression, obsessive compulsive disorder, sleep disorders, neurodegenerative disorders (such as head trauma or stroke), feeding disorders (such as anorexia or bulimia), schizophrenia, memory loss, disorders associated with withdrawal from drug or nicotine abuse, or the like or certain gastrointestinal disorders such as irritable bowel syndrome. Accordingly, the present invention provides a method for the treatment of a disorder of the central nervous system related to or affected by the 5-HT6 receptor in a patient in need thereof which comprises providing said patient a therapeutically effective amount of a compound of formula I as described hereinabove. The compounds may be provided by oral or parenteral administration or in any common manner known to be an effective administration of a therapeutic agent to a patient in need thereof.

The term "providing" as used herein with respect to providing a compound or substance embraced by the invention, designates either directly administering such a compound or substance, or administering a prodrug, derivative or analog which forms an equivalent amount of the compound or substance within the body.

The inventive method includes: a method for the treatment of schizophrenia; a method for the treatment of a disease associated with a deficit in memory, cognition, and/or learning or a cognitive disorder such as Alzheimer's disease or attention deficit disorder; a method for the treatment of developmental disorders such as schizophrenia; Down's syndrome, Fragile X syndrome, autism or the like; a method for the treatment of behavioral disorders, e.g., anxiety, depression, or obsessive compulsive disorder; a method for the treatment of motion or motor disorders such as Parkinson's disease or epilepsy; a method for the treatment of a neurodegenerative disorder such as stroke or head trauma or withdrawal from drug addiction including addiction to nicotine, alcohol, or other substances of abuse, or any other CNS disease or disorder associated with or related to the 5-HT6 receptor.

In one embodiment, the present invention provides a method for treating attention deficit disorders (ADD, also known as Attention Deficit Hyperactivity Disorder or ADHD) in both children and adults. Accordingly, in this embodiment, the present invention provides a method for treating attention deficit disorders in a pediatric patient.

The present invention therefore provides a method for the treatment of each of the conditions listed above in a patient, preferably in a human, said method comprises providing said patient a therapeutically effective amount of a compound of formula I as described hereinabove. The compounds may be provided by oral or parenteral administration or in any common manner known to be an effective administration of a therapeutic agent to a patient in need thereof.

The therapeutically effective amount provided in the treatment of a specific CNS disorder may vary according to the specific condition(s) being treated, the size, age and response pattern of the patient, the severity of the disorder, the judgment of the attending physician and the like. In general, effective amounts for daily oral administration may be about 0.01 to 1,000 mg/kg, preferably about 0.5 to 500 mg/kg and effective amounts for parenteral administration may be about 0.1 to 100 mg/kg, preferably about 0.5 to 50 mg/kg.

In actual practice, the compounds of the invention are provided by administering the compound or a precursor thereof in a solid or liquid form, either neat or in combination with one or more conventional pharmaceutical carriers or excipients. Accordingly, the present invention provides a pharmaceutical composition which comprises a pharmaceutically acceptable carrier and an effective amount of a compound of formula I as described hereinabove.

In one embodiment, the invention relates to compositions comprising at least one compound of formula I, or a pharmaceutically acceptable salt thereof, and one or more pharmaceutically acceptable carriers, excipients, or diluents. Such compositions include pharmaceutical compositions for treating or controlling disease states or conditions of the central nervous system. In certain embodiments, the compositions comprise mixtures of one or more compounds of formula I.

In certain embodiments, the invention relates to compositions comprising at least one compound of formula I, or a pharmaceutically acceptable salt thereof, and one or more pharmaceutically acceptable carriers, excipients, or diluents. Such compositions are prepared in accordance with acceptable pharmaceutical procedures. Pharmaceutically acceptable carriers are those carriers that are compatible with the other ingredients in the formulation and are biologically acceptable.

The compounds of formula I may be administered orally or parenterally, neat, or in combination with conventional pharmaceutical carriers. Applicable solid carriers can include one or more substances that can also act as flavoring agents, lubricants, solubilizers, suspending agents, fillers, glidants, compression aids, binders, tablet-disintegrating agents, or encapsulating materials. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

In certain embodiments, a compound of formula I is provided in a disintegrating tablet formulation suitable for pediatric administration.

Liquid carriers can be used in preparing solutions, suspensions, emulsions, syrups and elixirs. The active ingredient can be dissolved or suspended in a pharmaceutically acceptable liquid carrier such as water, an organic solvent, a mixture of both, or a pharmaceutically acceptable oil or fat. The liquid carrier can contain other suitable pharmaceutical additives such as, for example, solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration, the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

In certain embodiments, a liquid pharmaceutical composition is provided wherein said composition is suitable for pediatric administration. In other embodiments, the liquid composition is a syrup or suspension.

Liquid pharmaceutical compositions that are sterile solutions or suspensions can be administered by, for example, intramuscular, intraperitoneal or subcutaneous injection. Sterile solutions can also be administered intravenously. Compositions for oral administration can be in either liquid or solid form.

The compounds of formula I may be administered rectally or vaginally in the form of a conventional suppository. For administration by intranasal or intrabronchial inhalation or insufflation, the compounds of formula I can be formulated into an aqueous or partially aqueous solution, which can then be utilized in the form of an aerosol. The compounds of formula I can also be administered transdermally through the use of a transdermal patch containing the active compound and a carrier that is inert to the active compound, is non-toxic to the skin, and allows delivery of the agent for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the active ingredient can also be suitable. A variety of occlusive devices can be used to release the active ingredient into the blood stream such as a semipermeable membrane covering a reservoir containing the active ingredient with or without a carrier, or a matrix containing the active ingredient. Other occlusive devices are known in the literature.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The therapeutically effective amount of a compound of formula I provided to a patient will vary depending upon what is being administered, the purpose of the administration, such as prophylaxis or therapy, the state of the patient, the manner of administration, and the like. In therapeutic applications, compounds of formula I are provided to a patient suffering from a condition in an amount sufficient to treat or at least partially treat the symptoms of the condition and its complications. An amount adequate to accomplish this is a "therapeutically effective amount" as described previously herein. The dosage to be used in the treatment of a specific case must be subjectively determined by the attending physician. The variables involved include the specific condition and the size, age, and response pattern of the patient. The treatment of substance abuse follows the same method of subjective drug administration under the guidance of the attending physician. Generally, a starting dose is about 5 mg per day with gradual increase in the daily dose to about 150 mg per day, to provide the desired dosage level in the patient.

In certain embodiments, the present invention is directed to prodrugs of compounds of formula I. The term "prodrug," as used herein, means a compound that is convertible in vivo by metabolic means (e.g. by hydrolysis) to a compound of formula I. Various forms of prodrugs are known in the art such as those discussed in, for example, Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991), Bundgaard, et al., Journal of Drug Delivery Reviews, 8:1-38(1992), Bundgaard, J. of Pharmaceutical Sciences, 77:285 et seq. (1988); and Higuchi and Stella (eds.) Prodrugs as Novel Drug Delivery Systems, American Chemical Society (1975).

For a more clear understanding, and in order to illustrate the invention more clearly, specific examples thereof are set forth hereinbelow. The following examples are merely illustrative and are not to be understood as limiting the scope and underlying principles of the invention in any way. The term HNMR designates proton nuclear magnetic resonance. The term MS desigates mass spectrum. The terms THF, EtOAc, DMF and DMSO designate tetrahydrofuran, ethyl acetate, dimethyl formamide and dimethylsulfoxide, respectively. All chromatography is performed using $SiO_2$ as support. Unless otherwise noted, all parts are parts by weight.

EXAMPLE 1

Preparation of
1-(2-Chloro-1-chloromethyl-ethoxy)-2-nitro-benzene

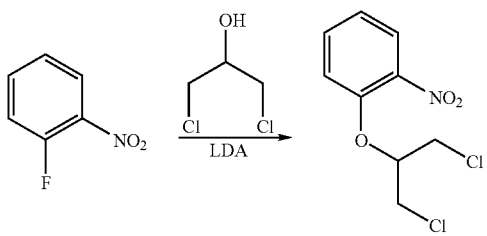

A solution of 1,3-dichloro-propan-2-ol (1.29 g, 10 mmoles) in THF, under nitrogen, was cooled to 0° C., treated dropwise with llithium diisopropylamide (LDA) (5 ml, 2M solution in hexanes, 10 mmoles), while maintaining the temperature constant at 0° C., stirred at 0° C. for 15 minutes, treated with 1-fluoro-2-nitro-benzene (1.2 g ml, 8.5 mmoles) and stirred at room temperature overnight. The reaction mixture was diluted with water and extracted with EtOAc. The extracts were combined, washed with brine, dried over $Na_2SO_4$, and concentrated under vacuum, to afford the title compound as an off-white solid (2.0 g, 8 mmoles), identified by HNMR analysis.

EXAMPLE 2

Preparation of 1-[3-(2-Chloro-1-chloromethyl-ethoxy)-2-nitro-phenylmethane-sulfonyl]-naphthalene

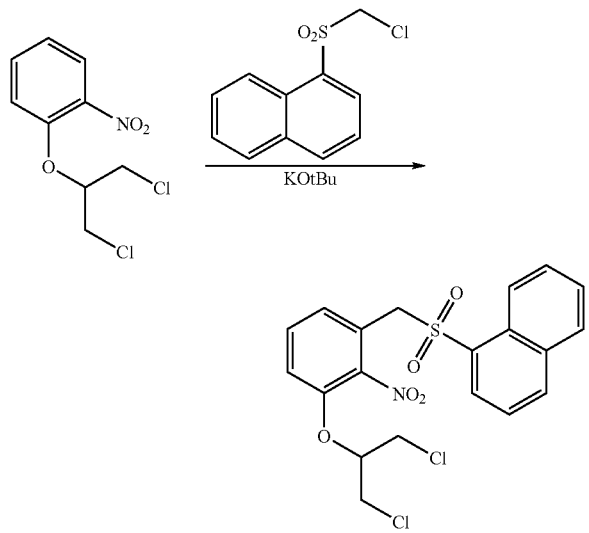

A mixture of 1-(2-chloro-1-chloromethyl-ethoxy)-2-nitro-benzene (2) (2.0 g, 8 mmoles) and 1-chloromethane-sulfonyl-naphthalene (2.88 g, 12 mmoles) in THF at −78° C., under nitrogen, was treated dropwise over a 30 minute period with a solution of 1M potassium t-butoxide (18 ml, 18 mmoles). The reaction temperature was allowed to rise to −40° C. The reaction mixture was stirred at −40° C. for 5 hours poured into cold 2N HCl and extracted with EtOAc. The extracts were combined, dried over $Na_2SO_4$, and concentrated under vacuum. The resultant solid residue was recrystallized from $CH_2Cl_2$/hexane to afford the title compound as an off-white solid (2.4 g, 5.3 mmoles), identified by HNMR analysis.

EXAMPLE 3

Preparation of 2-(2-Chloro-1-chloromethyl-ethoxy)-6-(naphthalene-1-sulfonylmethyl)-phenylamine

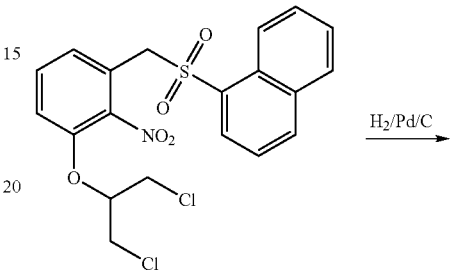

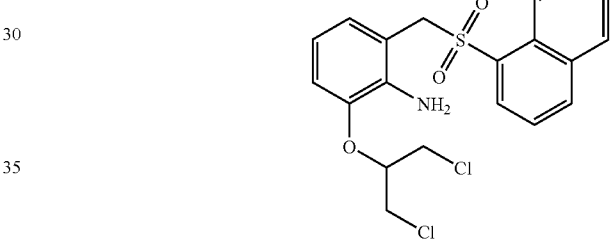

A mixture of 1-[3-(2-chloro-1-chloromethyl-ethoxy)-2-nitro-phenylmethanesulfonyl]-naphthalene (3) (2.4 g, 5.3 mmoles) and 10% Pd/C in a 1:1 mixture of THF and methanol was hydrogenated on a Parr hydrogenator at 40 lb/in² for 20 hours. The mixture was filtered through Celite. The filtrate was diluted with EtOAc, washed with water, dried over $Na_2SO_4$, and concentrated under vacuum to afford the title compound as an off white solid (2.02 g, 4.77 mmoles), identified by HNMR analysis.

EXAMPLE 4

Preparation of 7-(2-Chloro-1-chloromethyl-ethoxy)-3-(naphthalene-1-sulfonyl)-1H-indazole

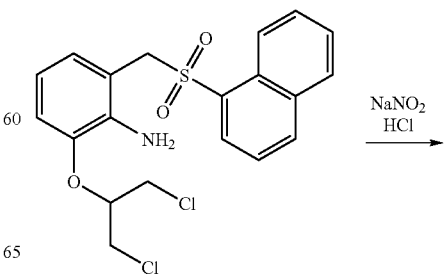

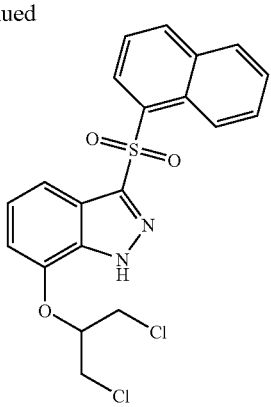

A mixture of 2-(2-chloro-1-chloromethyl-ethoxy)-6-(naphthalene-1-sulfonylmethyl)-phenylamine (4) (2 g, 4.77 mmoles) in THF and 4M HCl (15 ml) was stirred, under nitrogen, at 3° C., treated dropwise with a solution of sodium nitrite (0.34 g, 5 mmoles) in $H_2O$ (2 ml). The reaction mixture was poured into a cold solution of saturated sodium bicarbonate and extracted with EtOAc. The extracts were combined, dried over $Na_2SO_4$ and concentrated under vacuum to afford the title compound as an off white solid (1.76 g, 4.05 mmoles), identified by HNMR analysis.

EXAMPLE 5

Preparation of 7-Chloromethyl-2(naphthalene-1-sulfonyl)-7,8-dihydro-6-oxa-1,8a-diaza-acenaphthylene

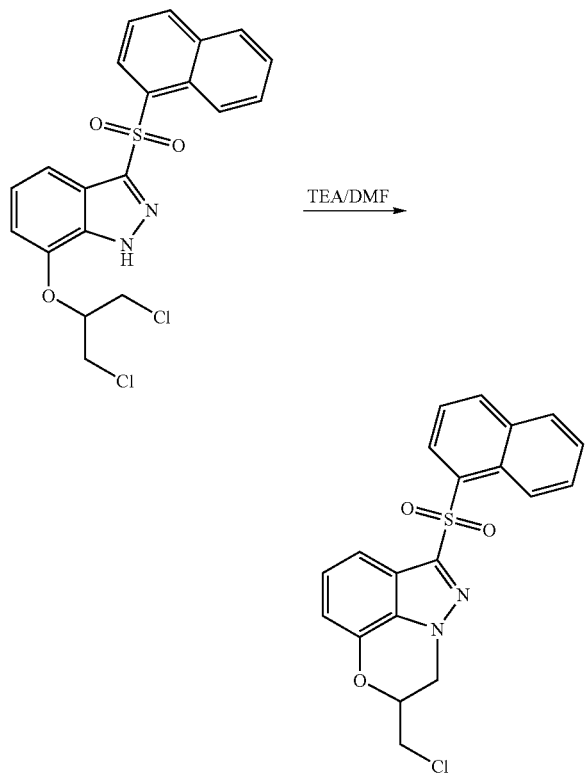

A mixture of 7-(2-chloro-1-chloromethyl-ethoxy)-3-(naphthalene-1-sulfonyl)-1H-indazole (5) (1.76 g, 4.05 mmoles) and triethylamine (0.7 ml, 4.05 mmoles) in DMF was stirred overnight at 70° C., cooled to room temperature, diluted with water and extracted with EtOAc. The extracts were combined, washed sequentially with water and brine, dried over $Na_2SO_4$ and concentrated under vacuum to afford the title compound (1.5 g, 3.85 mmoles), identified by HNMR analysis.

EXAMPLE 6

Preparation of N,N-dimethyl-1-[6-(1-naphthylsulfonyl)-2,3-dihydro[1,4]oxazino[2,3,4-hi]indazol-2-yl]methanamine Hydrochloride

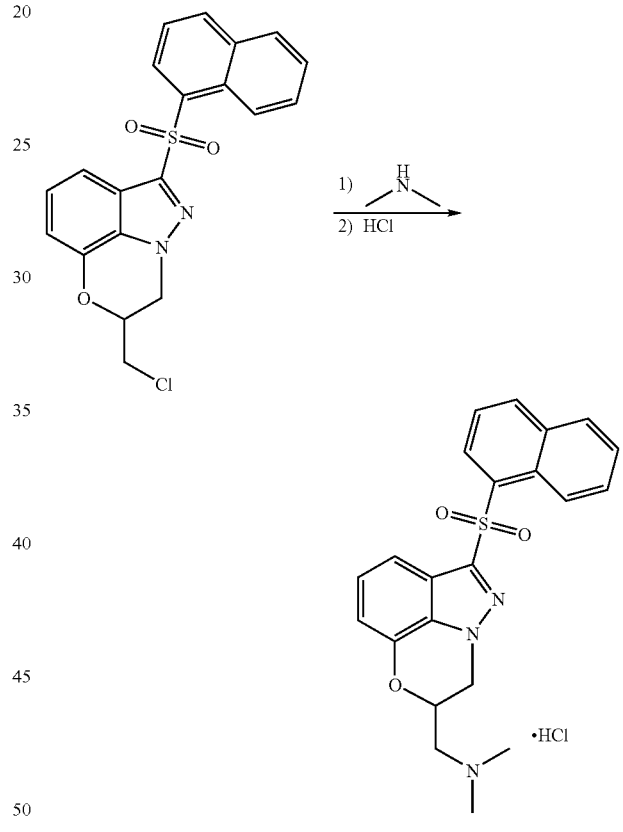

A mixture of 7-chloromethyl-2-(naphthalene-1-sulfonyl)-7,8-dihydro-6-oxa-1,8a-diaza-acenaphthylene (0.075 g, 0.18 mmoles) and dimethylamine (0.56 ml, 1M solution in THF, 0.56 mmoles) in DMSO was stirred under nitrogen at 100° C. for 4 hours, cooled to room temperature, diluted with water and extracted with EtOAc. The extracts were combined, washed sequentially with water and brine, dried over $Na_2SO_4$ and concentrated under vacuum. The resultant residue was purified by flash chromatography using as eluent 5% $CH_3OH$/EtOAc. The purified compound was dissolved in methanol, treated with 1M HCl in ether (0.2 ml, 0.2 mmoles) and evaporated to dryness to afford the title compound, MS: (ES) m/z 407.

EXAMPLE 7
Preparation of 6-(1-Naphthylsulfonyl)-2-(Pyrrolidin-1-1ylmethyl)-2,3-dihydro[1,4]oxazino[2,3,4-hi]indazole Hydrochloride

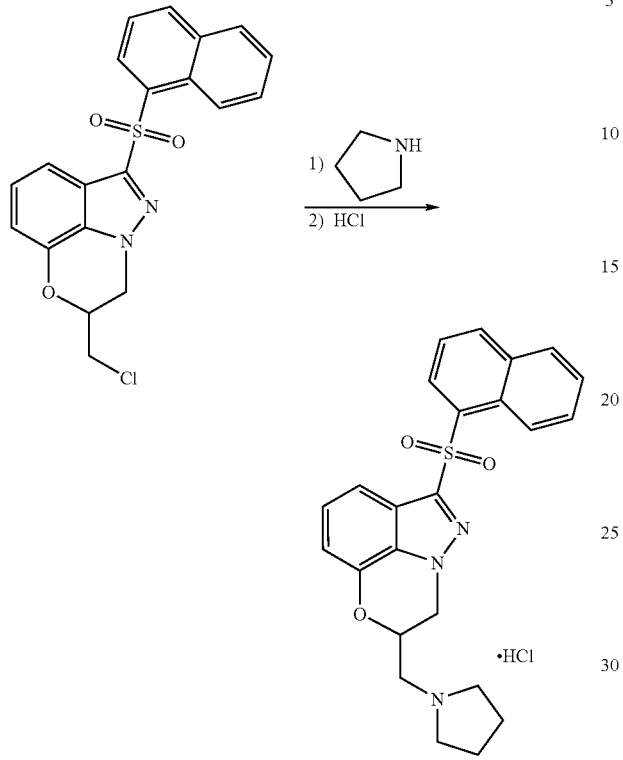

A mixture of 7-chloromethyl-2-(naphthalene-1-sulfonyl)-7,8-dihydro-6-oxa-1,8a-diaza-acenaphthylene (0.075 g, 0.18 mmoles) and pyrrolidine (0.04 g, 0.56 mmoles) in DMSO was stirred under nitrogen at 100° C. for 4 hours, cooled to room temperature, diluted with water and extracted with EtOAc. The extracts were combined, washed sequentially with water and brine, dried over $Na_2SO_4$ and concentrated under vacuum. The resultant residue was purified by flash chromatography using as eluent 5% $CH_3OH$/EtOAc. The purified compound was dissolved in methanol, treated with 1M HCl in ether (0.2 ml, 0.2 mmoles) and evaporated to dryness to afford the title compound, MS: (ES) m/z 433.

EXAMPLE 7
Preparation of 6-(1-Naphthylsulfonyl)-2-(piperidin-1-1ylmethyl)-2,3-dihydro[1,4]oxazino[2,3,4-hi]indazole Hydrochloride

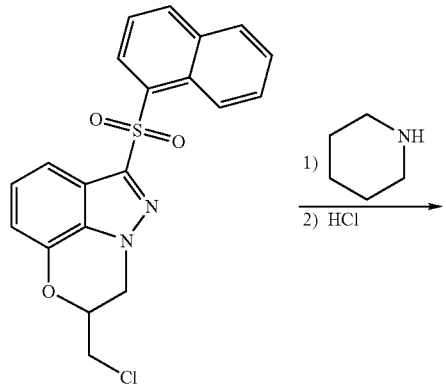

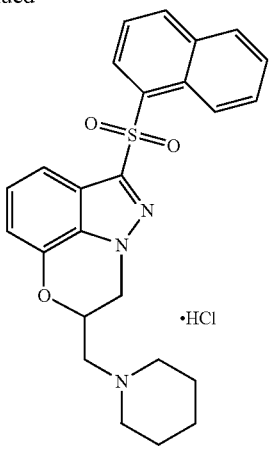

A mixture of 7-chloromethyl-2-(naphthalene-1-sulfonyl)-7,8-dihydro-6-oxa-1,8a-diaza-acenaphthylene (0.075 g, 0.18 mmoles) and piperidine (0.05 g, 0.56 mmoles) in DMSO was stirred under nitrogen at 100° C. for 4 hours, cooled to room temperature, diluted with water and extracted with EtOAc. The extracts were combined, washed sequentially with water and brine, dried over $Na_2SO_4$ and concentrated under vacuum. The resultant residue was purified by flash chromatography using as eluent 5% $CH_3OH$/EtOAc. The purified compound was dissolved in methanol, treated with 1M HCl in ether (0.2 ml, 0.2 mmoles) and concentrated to dryness to afford the title compound, MS: (ES) m/z 447.

EXAMPLE 9

Comparative Evaluation of 5-$HT_6$ Binding Affinity of Test Compounds

The affinity of test compounds for the serotonin 5-$HT_6$ receptor was evaluated in the following manner. Cultured Hela cells expressing human cloned 5-$HT_6$ receptors were harvested and centrifuged at low speed (1,000×g) for 10.0 minutes to remove the culture media. The harvested cells were suspended in half volume of fresh physiological phosphate buffered saline solution and recentrifuged at the same speed. This operation was repeated. The collected cells were then homogenized in ten volumes of 50 mM Tris.HCl (pH 7.4) and 0.5 mM EDTA. The homogenate was centrifuged at 40,000×g for 30.0 min and the precipitate was collected. The obtained pellet was resuspended in 10 volumes of Tris.HCl buffer and recentrifuged at the same speed. The final pellet was suspended in a small volume of Tris.HCl buffer and the tissue protein content was determined in aliquots of 10-25 μl volumes. Bovine Serum Albumin was used as the standard in the protein determination according to the method described in Lowry et al., *J. Biol. Chem.*, 193: 265 (1951). The volume of the suspended cell membranes was adjusted to give a tissue protein concentration of 1.0 mg/ml of suspension. The prepared membrane suspension (10 times concentrated) was aliquoted in 1.0 ml volumes and stored at −70° C. until used in subsequent binding experiments.

Binding experiments were performed in a 96 well microtiter plate format, in a total volume of 200 μl. To each well was added the following mixture: 80.0 μl of incubation buffer made in 50 mM Tris.HCl buffer (pH 7.4) containing 10.0 mM $MgCl_2$ and 0.5 mM EDTA and 20 μl of [$^3$H]-LSD (S.A., 86.0 Ci/mmol, available from Amersham Life Science), 3.0 nM. The dissociation constant, $K_D$ of the [$^3$H]LSD at the human serotonin 5-HT$_6$ receptor was 2.9 nM, as determined by saturation binding with increasing concentrations of [$^3$H]LSD. The reaction was initiated by the final addition of 100.0 μl of tissue suspension. Nonspecific binding was measured in the presence of 10.0 μM methiothepin. The test compounds were added in 20.0 μl volume.

The reaction was allowed to proceed in the dark for 120 minutes at room temperature, at which time, the bound ligand-receptor complex was filtered off on a 96 well unifilter with a Packard Filtermate® 196 Harvester. The bound complex caught on the filter disk was allowed to air dry and the radioactivity is measured in a Packard TopCount® equipped with six photomultiplier detectors, after the addition of 40.0 μl Microscint®-20 scintillant to each shallow well. The unifilter plate was heat-sealed and counted in a PackardTop-Count® with a tritium efficiency of 31.0%.

Specific binding to the 5-HT$_6$ receptor was defined as the total radioactivity bound less the amount bound in the presence of 10.0 μM unlabeled methiothepin. Binding in the presence of varying concentrations of test compound was expressed as a percentage of specific binding in the absence of test compound. The results were plotted as log % bound versus log concentration of test compound. Nonlinear regression analysis of data points with a computer assisted program Prism® yielded both the IC$_{50}$ and the K$_i$ values of test compounds with 95% confidence limits. A linear regression line of data points was plotted, from which the IC$_{50}$ value is determined and the K$_i$ value is determined based upon the following equation:

$$K_i = IC_{50}/(1+L/K_D)$$

where L was the concentration of the radioactive ligand used and K$_D$ is the dissociation constant of the ligand for the receptor, both expressed in nM.

Using this assay, the following Ki values were determined. The data are shown in Table I, below.

TABLE I

| Test Compound (Example No.) | 5-HT$_6$ Binding Ki (nM) |
| --- | --- |
| 6 | 1.6 |
| 7 | 3.0 |
| 8 | 160 |

| Comparative Examples | 5-HT6 Binding Ki (nM) |
| --- | --- |
| Clozapine | 6.0 |
| Loxapine | 41.4 |
| Bromocriptine | 23.0 |
| Methiothepin | 8.3 |
| Mianserin | 44.2 |
| Olanzepine | 19.5 |

What is claimed is:

1. A compound of formula I

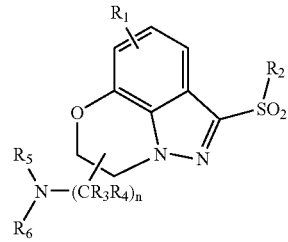

wherein

R$_1$ is H, halogen, CN, NO$_2$, OR$_7$, alkyl or haloalkyl;

R$_2$ is an alkyl, cycloalkyl, aryl or heteroaryl group each group optionally substituted or an optionally substituted 8- to 13-membered bicyclic or tricyclic ring system having a N atom at the bridgehead and optionally containing 1, 2 or 3 additional heteroatoms selected from N, O or S;

R$_3$ and R$_4$ are each independently H, or an optionally substituted alkyl group;

n is an integer of 1, 2, 3, 4, or 5;

R$_5$ and R$_6$ are each independently H or an alkyl, alkenyl, alkynyl or cycloalkyl, group each group optionally substituted or R$_5$ and R$_6$ may be taken together with the atom to which they are attached to form an optionally substituted 3- to 7-membered ring optionally containing an additional heteroatom selected from N, O or S; and R$_7$ is H, alkyl or haloalkyl; or a stereoisomer thereof or a pharmaceutically acceptable salt thereof, wherein the optional substituents are selected from the group consisting of halogen atoms, nitro, cyano, thiocyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsuiphonyl, carbamoyl, alkylamido, phenyl, phenoxy, benzyl, benzyloxy, heterocyclyl and cycloalkyl groups.

2. The compound according to claim 1 wherein wherein n is 1.

3. The compound according to claim 1 wherein R$_2$ is an optionally substituted aryl or heteroaryl group or an optionally substituted 8- to 13-membered bicyclic or tricyclic ring system having a N atom at the bridgehead and optionally containing 1, 2 or 3 additional heteroatoms selected from N, O or S.

4. The compound according to claim 1 wherein R$_5$ and R$_6$ are each independently H or alkyl or R$_5$ and R$_6$ are taken together with the atom to which they are attached to form an optionally substituted 3- to 7-membered ring.

5. The compound according to claim 2 wherein R$_1$ is H, halogen or C$_1$-C$_3$ alkyl.

6. The compound according to claim 2 wherein R$_2$ is an optionally substituted aryl or heteroaryl group and R$_3$ and R$_4$ are H.

7. The compound according to claim 6 wherein R$_5$ and R$_6$ are each independently H or alkyl or R$_5$ and R$_6$ are taken together with the atom to which they are attached to form an optionally substituted 3- to 5-membered ring.

8. The compound according to claim 7 wherein R$_2$ is naphthyl.

9. The compound according to claim 1 selected from the group consisting essentially of:

N,N-dimethyl-1-[6-(1-naphthylsulfonyl)-2,3-dihydro[1,4]oxazino[2,3,4-hi]indazol-2-yl]-methanamine;
6-(1-naphthylsulfonyl)-2-(pyrrolidin-1-1ylmethyl)-2,3-dihydro[1,4]oxazino[2,3,4-hi]-indazole;
6-(1-naphthylsulfonyl)-2-(piperidin-1-1ylmethyl)-2,3-dihydro[1,4]oxazino[2,3,4-hi]-indazole;
1-[6-(1-naphthylsulfonyl)-2,3-dihydro[1,4]oxazino[2,3,4-hi]indazol-2-yl]-methan-amine;
a stereoisomer thereof; and
a pharmaceutically acceptable salt thereof.

10. A method for the treating an attention deficit disorder in a patient in need thereof which comprises providing to said patient a therapeutically effective amount of a compuond of formula I

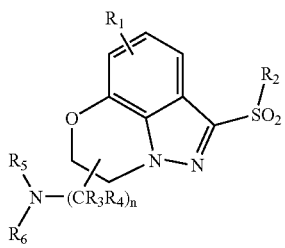

wherein
$R_1$ is H, halogen, CN, $NO_2$, $OR_7$, alkyl or haloalkyl;
$R_2$ is an alkyl, cycloalkyl, aryl or heteroaryl group each group optionally substituted or an optionally substituted 8- to 13-membered bicyclic or tricyclic ring system having a N atom at the bridgehead and optionally containing 1,2 or 3 additional heteroatoms selected from N, O or S;
$R_3$ and $R_4$ are each independently H, or an optionally substituted alkyl group;
n is an integer of 1, 2, 3, 4, or 5;
$R_5$ and $R_6$ are each independently H or an alkyl, alkenyl, alkynyl or cycloalkyl, group each group optionally substituted or $R_5$ and $R_6$ may be taken together with the atom to which they are attached to form an optionally substituted 3- to 7-membered ring optionally containing an additional heteroatom selected from N, O or S; and
$R_7$ is H, alkyl or haloalkyl; or
a stereoisomer thereof or a pharmaceutically acceptable salt thereof, wherein the optional substituents are selected from the group consisting of halogen atoms, nitro, cyano, thiocyanato, hydroxyl, alkyl, haloalkyl, alkoxy, haloalkoxy, amino, alkylamino, dialkylamino, formyl, alkoxycarbonyl, carboxyl, alkanoyl, alkylthia, alkylsulphinyl, alkylsulphonyl, carbamoyl, alkylamido, phenyl, phenoxy, benzyl, benzyloxy, heterocyclyl and cycloalkyl groups.

11. A pharmaceutical composition which comprises a pharmaceutically acceptable carrier and an effective amount of a compound of formula I

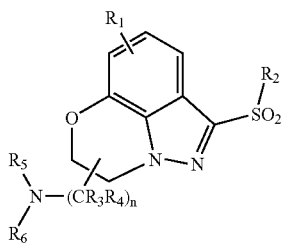

wherein
$R_1$ is H, halogen, CN, $NO_2$, $OR_7$, alkyl or haloalkyl;
$R_2$ is an alkyl, cycloalkyl, aryl or heteroaryl group each group optionally substituted or an optionally substituted 8- to 13-membered bicyclic or tricyclic ring system having a N atom at the bridgehead and optionally containing 1,2 or 3 additional heteroatoms selected from N, O or S;
$R_3$ and $R_4$ are each independently H, or an optionally substituted alkyl group;
n is an integer of 1, 2, 3, 4, or 5;
$R_5$ and $R_6$ are each independently H or an alkyl, alkenyl, alkynyl or cycloalkyl, group each group optionally substituted or $R_5$ and $R_6$ may be taken together with the atom to which they are attached to form an optionally substituted 3- to 7-membered ring optionally containing an additional heteroatom selected from N, O or S; and
$R_7$ is H, alkyl or haloalkyl; or
a stereoisomer thereof or a pharmaceutically acceptable salt thereof, wherein the optional substituents are selected from the group consisting of halogen atoms, nitro, cyano, thiocyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl, alkylamido, phenyl, phenoxy, benzyl, benzyloxy, heterocyclyl and cycloalkyl groups.

12. The composition according to claim 11 having a formula I compound wherein n is 1.

13. The composition according to claim 12 having a formula I compound wherein $R_2$ is an optionally substituted aryl or heteroaryl group or an optionally subtituted 8- to 13-membered bicyclic or tricyclic ring system having a N atom at the bridgehead and optionally containing 1, 2 or 3 additional heteroatoms selected from N, O or S.

14. The composition according to claim 13 having a formula I compound wherein $R_5$ and $R_6$ are each independently H or alkyl or $R_5$ and $R_6$ are taken together with the atom to which they are attached to form an optionally substituted 3- to 7-membered ring.

15. The composition according to claim 11 having a formula I compound selected from the group consisting of:

N,N-dimethyl-1-[6-(1-naphthylsulfonyl)-2,3-dihydro[1,4]oxazino[2,3,4-hi]indazol-2-yl]-methanamine;
6-(1-naphthylsulfonyl)-2-(pyrrolidin-1-1ylmethyl)-2,3-dihydro[1,4]oxazino[2,3,4-hi]-indazole;
6-(1-naphthylsulfonyl)-2-(piperidin-1-1ylmethyl)-2,3-dihydro[1,4]oxazino[2,3,4-hi]-indazole;
1-[6-(1-naphthylsulfonyl)-2,3-dihydro[1,4]oxazino[2,3,4-hi]indazol-2-yl]-methan-amine;
a stereoisomer thereof; and
a pharmaceutically acceptable salt thereof.

16. A process for the preparation of a compound of formula I

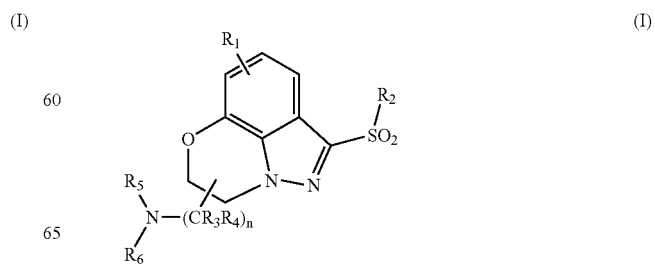

wherein

R₁ is H, halogen, CN, NO₂, OR₇, alkyl or haloalkyl;

R₂ is an alkyl, cycloalkyl, aryl or heteroaryl group each group optionally substituted or an optionally substituted 8- to 13-membered bicyclic or tricyclic ring system having a N atom at the bridgehead and optionally containing 1, 2 or 3 additional heteroatoms selected from N, O or S;

R₃ and R₄ are each independently H, or an optionally substituted alkyl group;

n is an integer of 1, 2, 3, 4, or 5;

R₅ and R₆ are each independently H or an alkyl, alkenyl, alkynyl or cycloalkyl, group each group optionally substituted or R₅ and R₆ may be taken together with the atom to which they are attached to form an optionally substituted 3- to 7-membered ring optionally containing an additional heteroatom selected from N, O or S; and R₇ is H, alkyl or haloalkyl;

wherein the optional substituents are selected from the group consisting of halogen atoms, nitro, cyano, thiocyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl, alkylamido, phenyl, phenoxy, benzyl, benzyloxy, heterocyclyl and cycloalkyl groups;

which process comprises reacting a compound of formula II

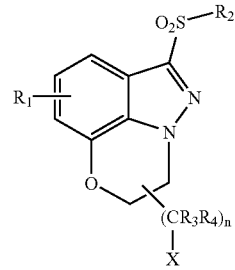

(II)

wherein R₁, R₂, R₃ and R₄ are as described for formula I and X is Cl, Br or I with an amine, HNR₅R₆, wherein R₅ and R₆ are as described for formula I, optionally in the presence of a solvent.

* * * * *

UNITED STATES PATENT AND TRADEMARK OFFICE
CERTIFICATE OF CORRECTION

PATENT NO. : 7,429,582 B2
APPLICATION NO. : 11/786314
DATED : September 30, 2008
INVENTOR(S) : Greenfield et al.

It is certified that error appears in the above-identified patent and that said Letters Patent is hereby corrected as shown below:

Column 23, line 13 replace text "A method for the treating an attention deficit disorder" with --A method for treating an attention deficit disorder--;

Column 23, line 51 replace "akylthia" with --alkylthio--.

Signed and Sealed this

Thirtieth Day of December, 2008

JON W. DUDAS
*Director of the United States Patent and Trademark Office*